(12) United States Patent
Jackman et al.

(10) Patent No.: US 8,568,443 B1
(45) Date of Patent: Oct. 29, 2013

(54) SURGICAL GRAPSER TOOL AND ACTUATION MECHANISM

(75) Inventors: Brian Jackman, Milwaukee, WI (US); Warren Taylor, Longmont, CO (US); David Newton, Longmont, CO (US)

(73) Assignee: Encision, Inc., Boulder, CO (US)

( * ) Notice: Subject to any disclaimer, the term of this patent is extended or adjusted under 35 U.S.C. 154(b) by 946 days.

(21) Appl. No.: 12/469,842

(22) Filed: May 21, 2009

Related U.S. Application Data

(60) Provisional application No. 61/055,064, filed on May 21, 2008.

(51) Int. Cl.
*A61B 17/00* (2006.01)

(52) U.S. Cl.
USPC ............... 606/205; 606/157; 606/51; 606/52

(58) Field of Classification Search
USPC ............ 606/205, 206, 207, 51, 52, 157, 208, 606/209, 210, 211; 81/300, 345; 294/116
See application file for complete search history.

(56) References Cited

U.S. PATENT DOCUMENTS

| | | | | |
|---|---|---|---|---|
| 5,301,533 A * | 4/1994 | Jackson | ............. | 72/328 |
| 5,752,973 A | 5/1998 | Kieturakis | | |
| 6,582,451 B1 * | 6/2003 | Marucci et al. | ............. | 606/207 |
| 7,032,944 B2 * | 4/2006 | Moilanen et al. | ............. | 294/203 |
| 2005/0165429 A1 * | 7/2005 | Douglas et al. | ............. | 606/157 |

* cited by examiner

*Primary Examiner* — Gary Jackson
*Assistant Examiner* — Katrina Stransky
(74) *Attorney, Agent, or Firm* — Neugeboren O'Dowd PC

(57) ABSTRACT

A surgical instrument and actuation mechanism comprises an end effector, the end effector including opposing faces, and a positioning slot. The positioning slot includes a linear portion and a radial portion. In accordance with one aspect, the surgical instrument further comprises an actuation mechanism engaged with the positioning slot, wherein the opposing faces of the end effector move in a parallel manner when the actuation mechanism moves within the linear portion of the positioning slot, and wherein the opposing faces of the end effector move in an angular manner when the actuation mechanism moves within the radial portion of the positioning slot.

15 Claims, 15 Drawing Sheets

SURGICAL GRAPSER TOOL AND ACTUATION MECHANISM

PRIORITY AND RELATED APPLICATIONS

This application claims the benefit of Provisional U.S. Application No. 61/055,064 filed on May 21, 2008. The details of Application No. 61/055,064 are incorporated by reference into the present application in its entirety and for all purposes.

FIELD OF THE INVENTION

Aspects of the present invention relate to surgical instruments including those used for minimally invasive and for open procedures. The instruments may include features that enable them to be used in conjunction with monopolar and/or bipolar electrosurgical energy sources. In particular, but not by way of limitation, aspects of the present invention relate to a grasper for attachment to and use with surgical instrument assemblies.

BACKGROUND

Surgical tools employing jaws with substantially parallel faces allow a user to apply a more uniform grasping pressure across tissue than with conventional (angular motion) graspers. The geometry of angular motion graspers causes the base of the jaws to compress tissue much tighter than the tips of the jaws, for a given handle force applied, due to the difference in distance from the fulcrum. When grasper jaws are partially open, angular motion jaws have a much larger space between jaws at the tip than at the base of the jaw, while a parallel jaw has the same width between the base of the jaw and the tip of jaw no matter what distance the jaws are apart. Therefore, if the jaws are full of tissue the parallel jaws would compress the tissue uniformly along its entire length while the angular motion jaws would compress the tissue at the base much more than at the tip.

The uniform distance between jaws in a parallel arrangement allows the user to have a more controlled manipulation of tissue. Depth perception and alignment of tissue with respect to the jaws is a lesser problem because the jaws are the same distance from each other along their entire length. The uniform distance and motion of parallel jaws eliminates any component of a force vector that would push tissue out of the jaws distally during closing. A parallel jaw design also allows for a more uniform coagulation of vessels because of the uniform compression of tissue between the jaws. For a given separation distance at the jaw tips, larger volumes of tissue may be grasped compared to an angular motion grasper.

A parallel jaw grasper will be less likely to become fouled with tissue from a prior coagulation when several coagulations are being performed in a sequence. This is because the jaws can be separated along their full length allowing tissue to be removed from one jaw using a second instrument (or by simply falling away). A conventional instrument tends to create a possibility for small amounts of tissue to become lodged near the proximal end of the jaw area.

However, there are also benefits to grasper configurations with an angular displacement of the jaws at the end of the opening motion. This allows the parallel jaws to get the tips much wider than is possible with a purely parallel motion. The angular displacement of the jaws allows effective grasping of tissue.

It would be beneficial to have a device that is capable of both parallel movement and angular movement in order to take advantage of the benefits associated with both configurations. For example, by adding an angular movement towards the end of the instrument motion, the jaws will more likely fit within a smaller trocar cannula but still open very wide at the tip to aid with dissection and get around larger tissue areas for grasping.

SUMMARY OF THE INVENTION

In accordance with one aspect a surgical instrument comprises an end effector, the end effector including opposing faces and adapted to perform a grasping motion, and an actuation mechanism engaged with the end effector. The opposing faces of the end effector are maintained in a substantially parallel manner for at least a first portion of the grasping motion, and the opposing faces of the end effector are maintained in a substantially angular manner for at least a second portion of the grasping motion.

In accordance with one aspect a surgical instrument comprises an end effector, the end effector including opposing faces and a positioning slot, the positioning slot including a linear portion and a radial portion. In accordance with other aspects the surgical instrument further comprises an actuation mechanism engaged with the positioning slot wherein the opposing faces of the end effector move in a parallel manner when the actuation mechanism moves within the linear portion of the positioning slot, and wherein the opposing faces of the end effector move in an angular manner when the actuation mechanism moves within the radial portion of the positioning slot.

In accordance with another aspect, a surgical instrument comprises a housing, an actuation rod extending through the housing, a jaw member, the jaw member including a positioning slot, the positioning slot including a linear portion and an radial portion. In accordance with other aspects, the surgical instrument further comprises an actuation link having a proximal end and a distal end, the proximal end of the actuation link coupled with the actuation rod, a pivot link having a proximal end and a distal end, the proximal end of the pivot link coupled with distal end of the actuation link, the distal end of the pivot link coupled with the jaw member, wherein the proximal end of the pivot link and the distal end of the actuation link are slidably engaged within the positioning slot.

In accordance with another aspect, a surgical instrument actuation device comprises an end effector, the end effector including a positioning slot, the positioning slot including a linear portion and a radial portion. The surgical instrument also includes an actuation link having a proximal end and a distal end, the proximal end of the actuation link coupled with an actuator of the surgical tool and a pivot link having a proximal end and a distal end, the proximal end of the pivot link coupled with distal end of the actuation link, the distal end of the pivot link coupled with the end effector. The proximal end of the pivot link and the distal end of the actuation link are slidably engaged with the positioning slot.

In accordance with another aspect, a surgical instrument, comprises a housing, the housing including a positioning slot, the positioning slot including a linear portion and a radial portion. The surgical instrument also includes an actuation rod, an end effector, the end effector including a cam portion, and an actuation link having a proximal end and a distal end, the proximal end of the actuation link coupled with the actuation rod, the distal end of the actuation link coupled with the end effector. The cam portion of the end effector is slidably engaged within the positioning slot.

Other aspects are disclosed herein and will become apparent to one of skill in the art when considered in conjunction with the drawings and description herein.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings, wherein:

DETAILED DESCRIPTION

The following figures and associated descriptions present several possible embodiments of various aspects of a device constructed in accordance with the present invention. However, it is not intended that the scope of the invention be limited by reference to any of the examples disclosed herein. Any reference to "the invention" is not meant to be limiting to the claims and all embodiments disclosed herein are meant to be representative of devices, methods, and other structure that are within the broad spirit and scope of the aspects disclosed.

In accordance with one aspect of a device constructed in accordance with the present invention, a surgical grasper tool or instrument is disclosed in which the opposing jaw faces move substantially parallel to each other for at least a portion of the grasping motion. During another portion of the instrument motion, the jaws move with a substantially angular displacement. When closed, the jaws are essentially and functionally parallel. When the jaws begin to open, they remain parallel for the main part of the motion. Then, towards a fully open position, the jaws change their motion to achieve an angular displacement as opposed to a linear displacement. In general, this allows a surgeon to have parallel motion for the main part of the grasping technique, but also allows the jaws to open wider at the tip to grasp more material.

Figure 1:
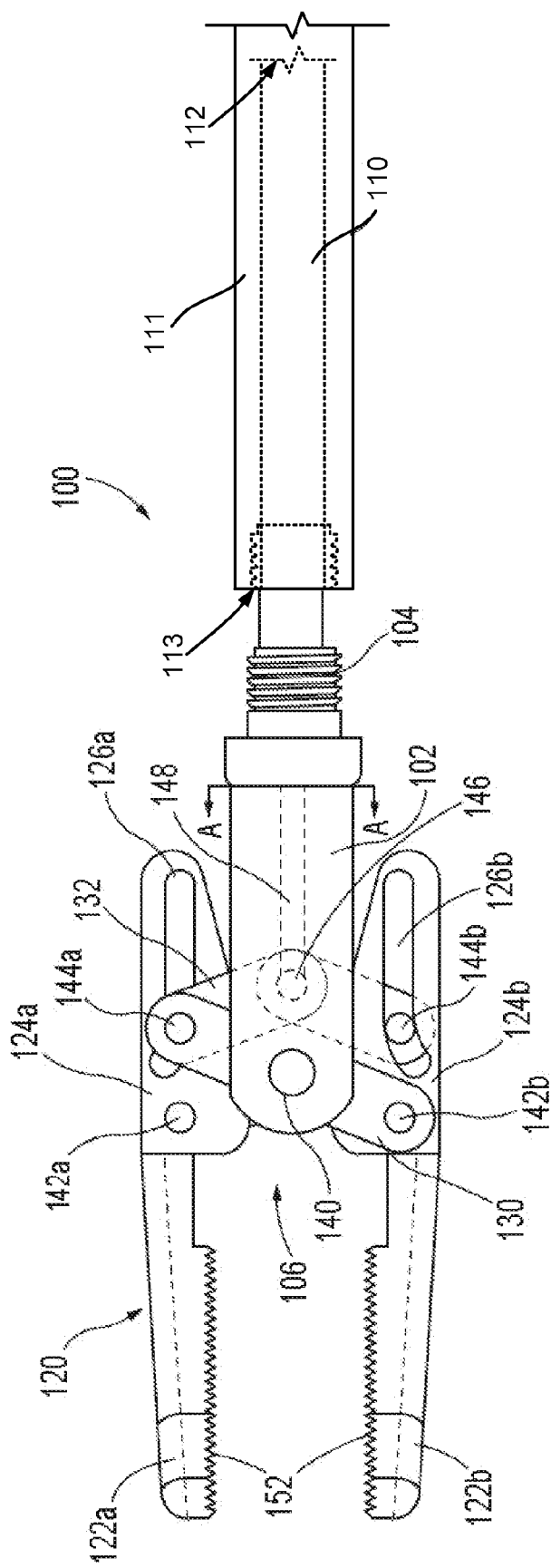
FIG. 1 is a side view of a device constructed in accordance with various aspects of the present invention.

The motion of the jaws (or other surgical end effector tools) can be accomplished in a variety of ways as described in conjunction with the Figures. For example, FIG. 1 illustrates one embodiment of a device constructed in accordance with aspects of the invention. Surgical tool 100 includes a housing 102 with a generally circular cross section. A proximal end 108 of the housing has a threaded portion 104 that is adapted to couple or otherwise engage with the distal end 113 of a larger instrument handle assembly 111 known in the art. For example, surgical tool 100 may couple with a handle assemblies made by companies such as Encision of Boulder, Colo.

Proximate to its distal end 106 the housing 102 couples with a fulcrum pin 140 as described in more detail below. An activation rod 110 extends through the housing 102 and couples at pin 146 with a device activation mechanism located partly within the housing 102. A proximal end 112 of the activation rod 110 is designed to extend through the handle assembly 111 in order for a user to easily activate and control the surgical tool 100, and more particularly, the opening and closing of jaws 122a and 122b. As described in more detail below, one or more sets of links, cams, and/or other mechanisms engage with the activation rod 110. In concert with the linear movement of the activation rod, the various types of mechanisms cause the parallel and/or angular movement of the grasper jaws or other end effectors located on the distal end of the tool 100.

In FIG. 1, a pair of generally opposing grasper jaws 120 are engaged with the actuation rod 110 via a series of links generally shown as 130 (pivot links) and 132 (actuation links). In the embodiment of FIG. 1, there are a pair of actuation links 132 and a pair of pivot links 130. The grasper jaws 120 are not required to have any specific configuration as the surgical tool 100 is contemplated to be of such a general configuration as to work with any known end effector such as graspers, scissors, clamps, ablation devices, and any other known surgical end effector tool. In the embodiment shown in FIG. 1, the grasper jaws 120 include opposing grasping members 122a and 122b that each include a gripping surface 152. Each of the members 122a and 122b are integrated with a mounting and control portion 124a and 124b respectively. As constructed, the mounting and control portions 124a and 124b may be integral with, or formed as separate parts from grasping members 122a and 122b. The mounting and control portions 124a and 124b generally include means for the grasper 120 to connect to and interact with the link mechanisms and actuation rod such that linear movement of the actuation rod will cause an opening and closing of the grasper. In the embodiment of FIG. 1, the mounting and control portions 124a and 124b of the grasper jaws 120 include slots 126a and 126b that aid in controlling the movement of the jaw faces 122a and 122b as well as connection points 142a and 142 that connect the pair of pivot links 130 to the mounting and control sections 124a and 124b.

Figure 2:
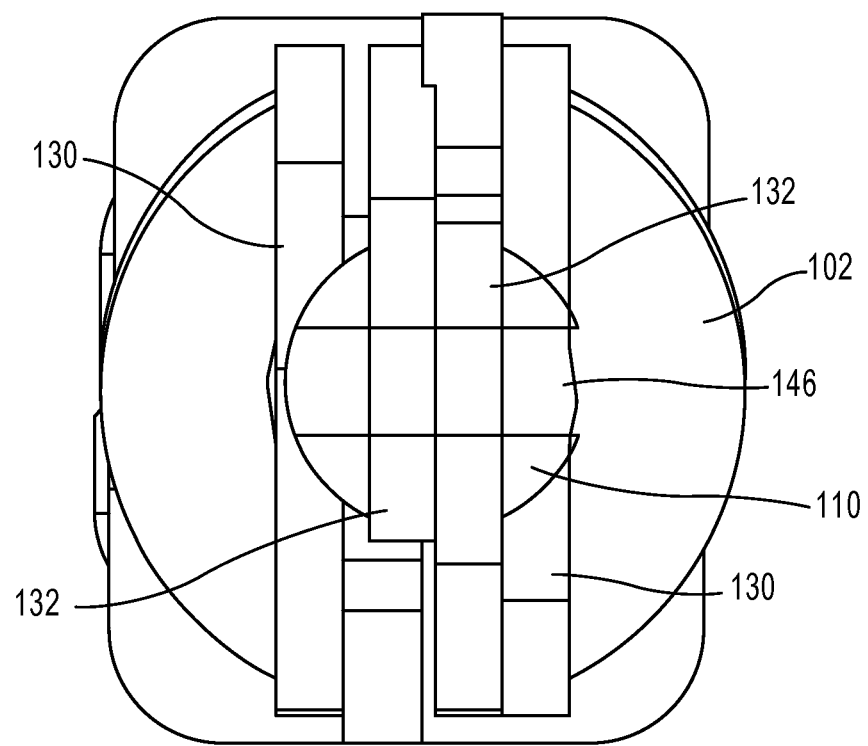
FIG. 2 is a perpendicular cross-section of the device shown in FIG. 1.

Connecting the actuation rod 110 and housing 102 to the grasper jaws 120 (e.g. the mounting portions 124a and 124b) are the pair of actuation links 132 and the pair of pivot links 130. The actuation links 132 include a proximal rotation point 146 that engages with the actuation rod 110 via a known connector such as a pin, hinge, pivot, etc. At a distal end of the actuation links 132 a pair of connectors 144a and 144b engage the actuation links with both the slots 126a and 126b as well as provide a proximal rotation point for the pair of pivot links 130. A distal end of the pivot links 130 includes a further pair of connectors 142a and 142b that engage with the mounting portions 124a and 124b of the grasper jaws 120. A fulcrum point 140 connects the pivot links together and also connects the pivot links with the housing 102. FIG. 2 shows a cross section of the device 100 in FIG. 1 along section lines A-A.

Figure 3A:
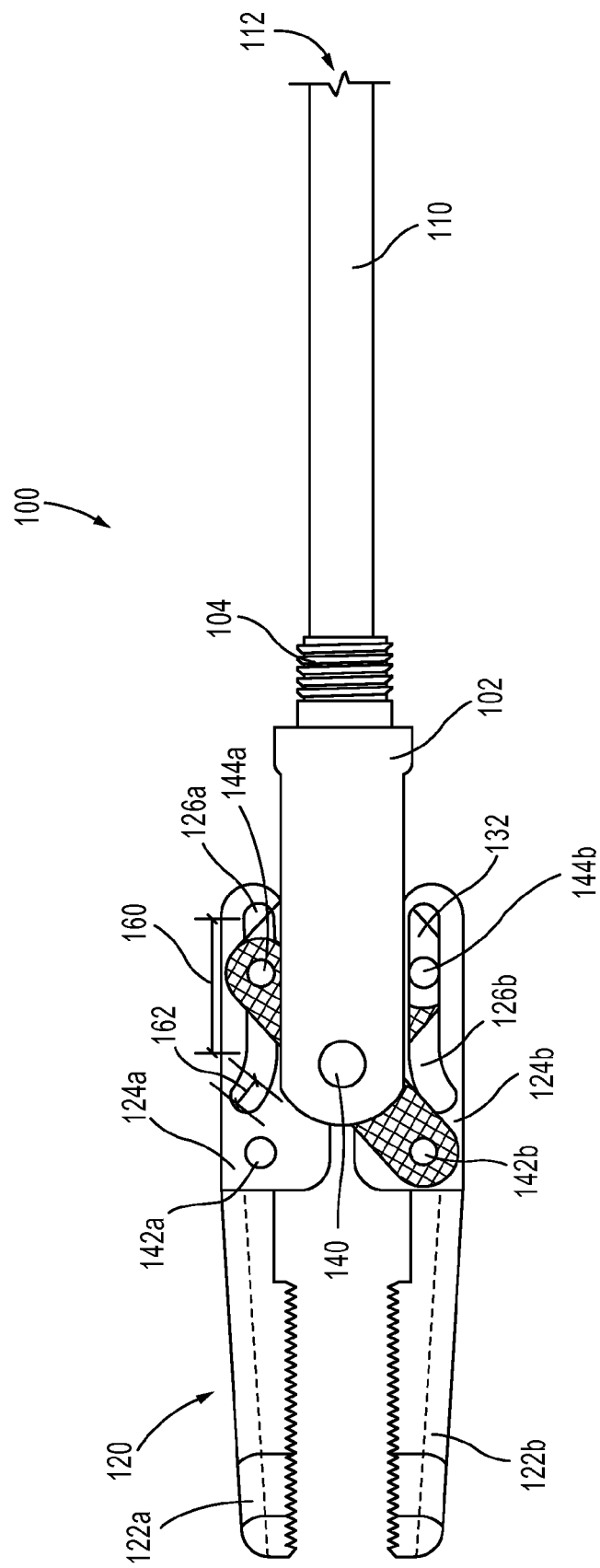
FIG. 3A is the device of FIG. 1 in a first position.
Figure 3B:
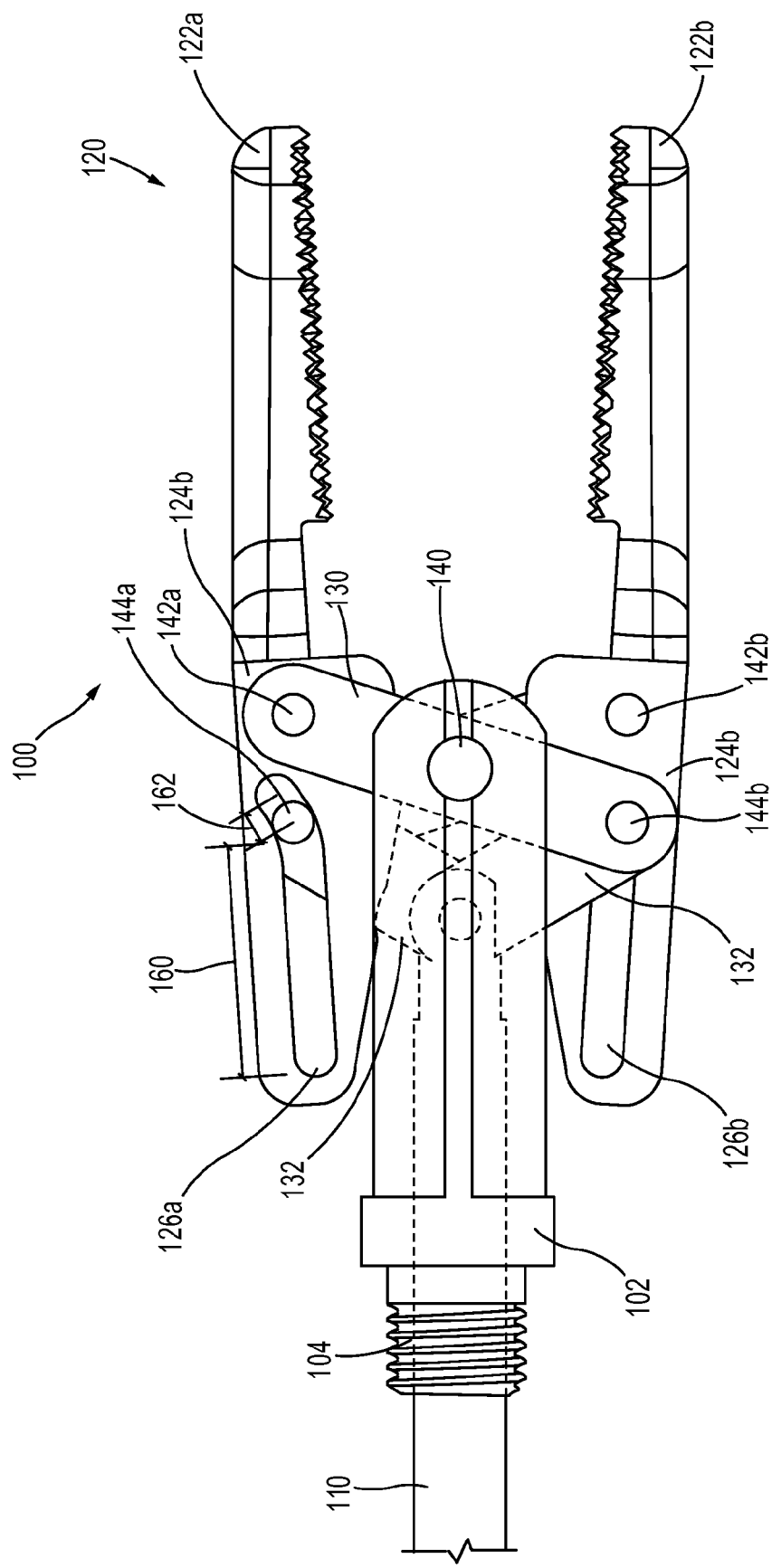
FIG. 3B is the device of FIG. 1 in a second position.
Figure 3C:
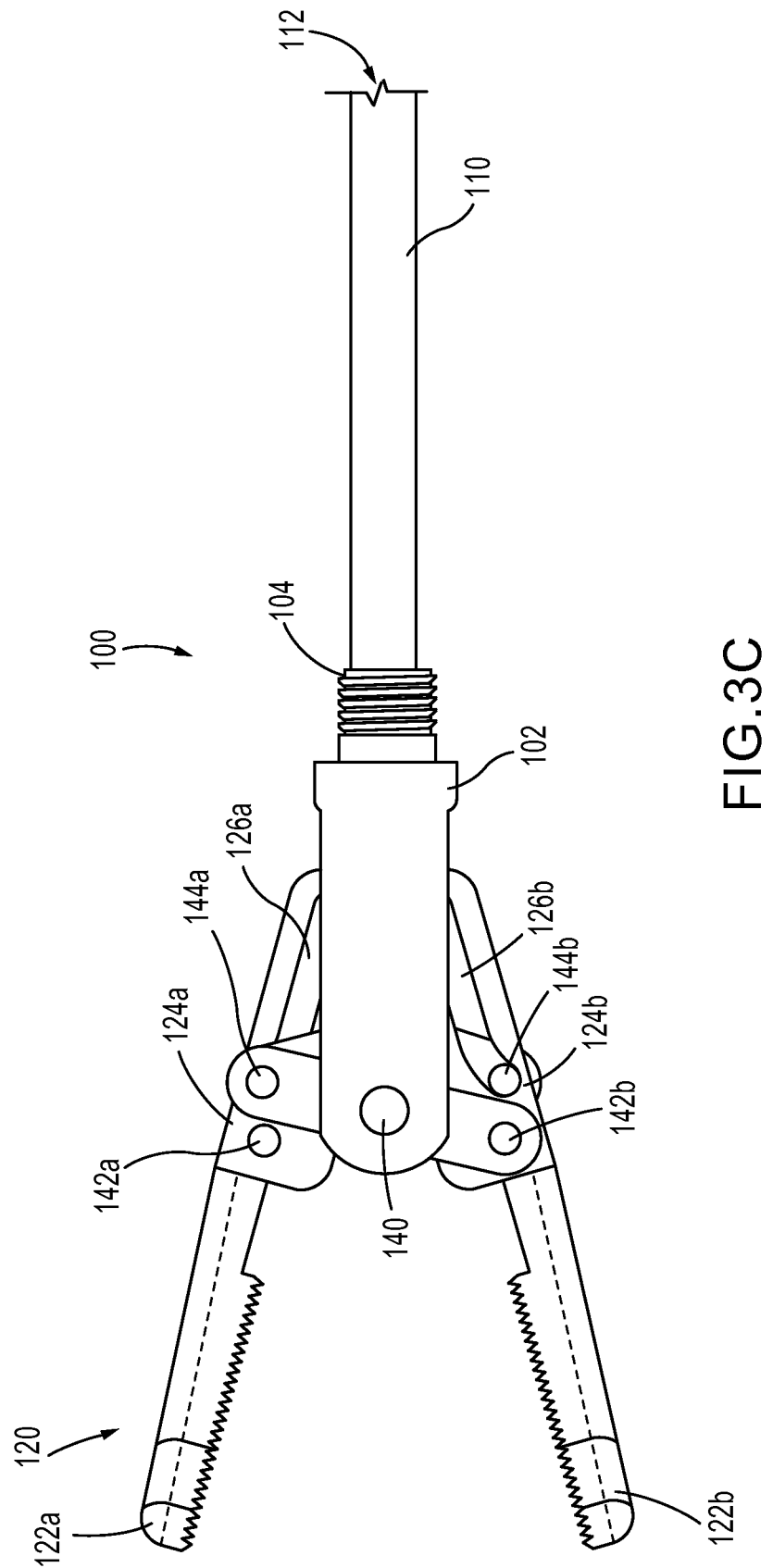
FIG. 3C is the device of FIG. 1 in a third position.

FIGS. 3A-3C show the surgical instrument 100 in various positions and demonstrates the combined linear and angular movement of the grasper jaws 120 corresponding to the linear movement of the actuation rod 110. As discussed below, the combined linear and angular movement of the grasper jaws 120 is accomplished by utilizing the slot(s) 126a and 126b as a guide for the connection points 144a and 144b between the actuation links 132 and pivot links 130.

Beginning with FIG. 3A the grasper jaws 120 are shown in a position where the jaw faces are substantially parallel to each other. The parallel movement of the grasper jaws is maintained while the connectors 144a and 144b are sliding in the linear section 160 of the slots 126a and 126b. FIG. 3B shows the point where the actuation rod 110 has moved in a distal direction such that the actuation links 132, and more specifically, the connectors 144a and 144b, are at the point where the radial section 162 of the slots 126a and 126b are engaged by the connectors 144a and 144b joining the actuation links 132 and the pivot links 130. When there is movement through the radial section 162, this causes a progressive angular displacement of the jaws 122a and 122b. FIG. 3C shows the position where the actuation rod 110 has been moved to its most distal position, and thus the connectors 144a and 144b have been moved to the extent of the radial portion 162 of the slots 126a and 126b. As a result, the angular displacement between the jaws 122a and 122b are increased as the actuation rod 110 pushes the connectors 144a and 144b through the radial section 162.

It will be appreciated that the shape of the slots 126a and 126b will substantially dictate the movement of the grasper jaws and the attribution of both parallel movement and angular movement. Thus, a device can be designed with a very specific series of grasper jaw movements based on the shape of the slots 126a and 126b.

Figure 4:
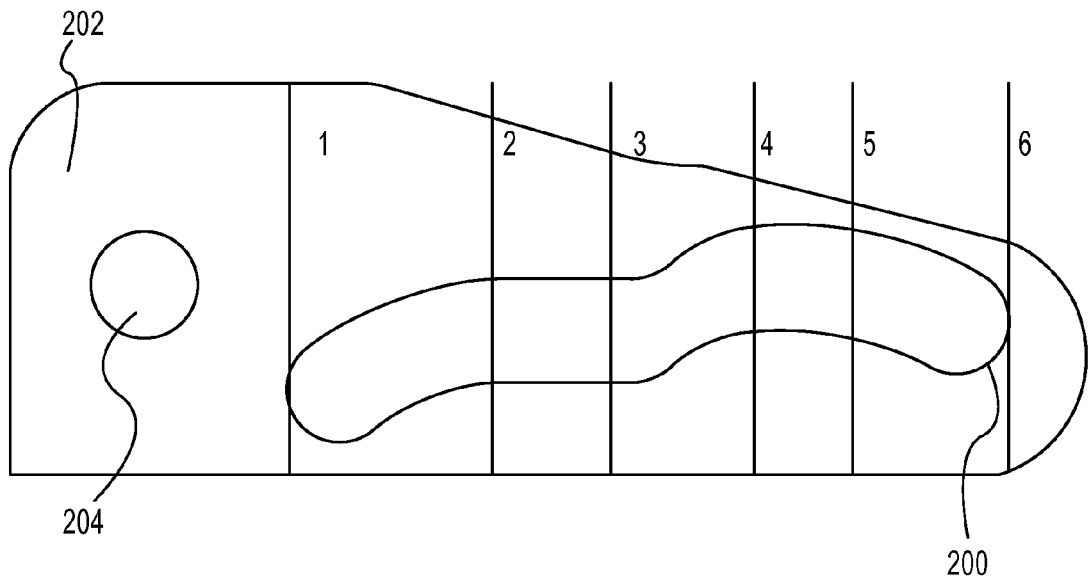
FIG. 4 is a detailed view of one embodiment of a portion of the grasper jaw mounting section.

FIG. 4 shows an alternate embodiment of a multi-section slot 200 that may be incorporated into the mounting and control portion 202 of a grasper jaw as shown in FIG. 1. For the purposes of the embodiment shown in connection with FIGS. 4-4G, only the slot 200 and its specific attributes are called out. All other components are similar to the embodiment shown in FIG. 1.

Figure 4A:
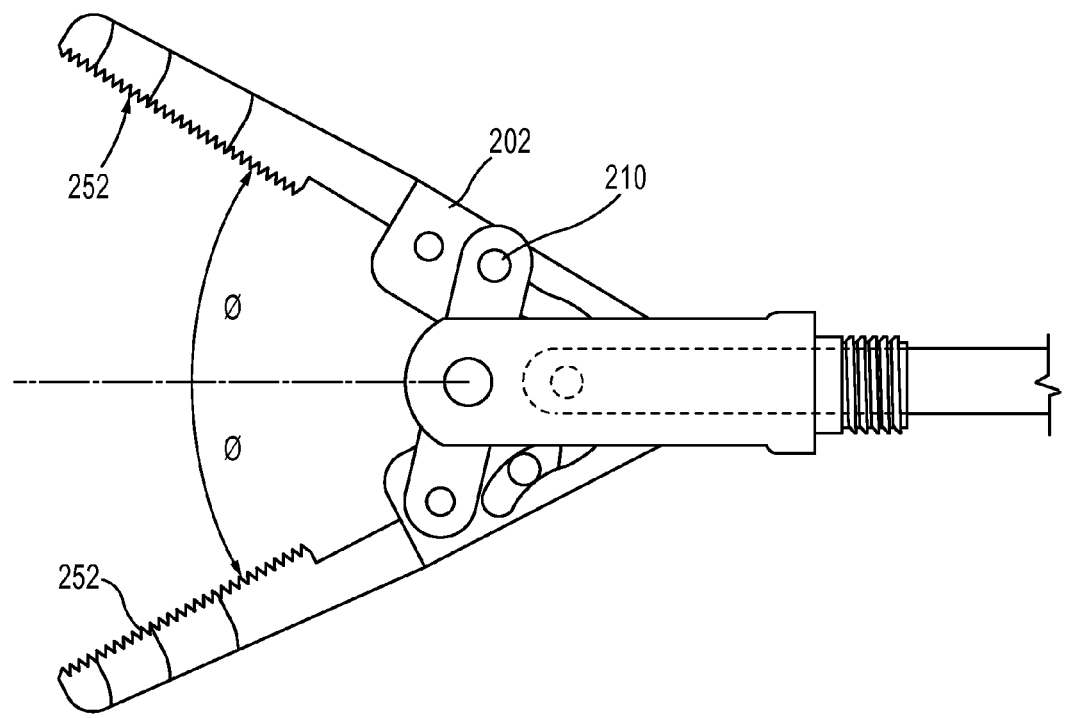
FIG. 4A shows another embodiment of a device constructed in accordance with aspects of the present invention in a first position.

In FIG. 4, a connection point 204 is also shown that connects to the distal end of a pivot link as previously described in conjunction with FIG. 1. In FIG. 4, the slot 200 includes five sections, labeled 1-5, and each with a specific geometry. In FIG. 4A, section 1 of the slot 200 is engaged by the connector 210 and represents a fully open position of the jaw faces 252 shown separated by an angle θ. As the actuation rod 110 is pulled and thus moves the connection between the actuation links and pivot links (210) through the radially shaped section 1, the jaws move in an angular motion, bringing them closer to a parallel configuration (i.e. θ is decreasing) as the rod moves toward the end of section 1 and the beginning of section 2.

Figure 4B:
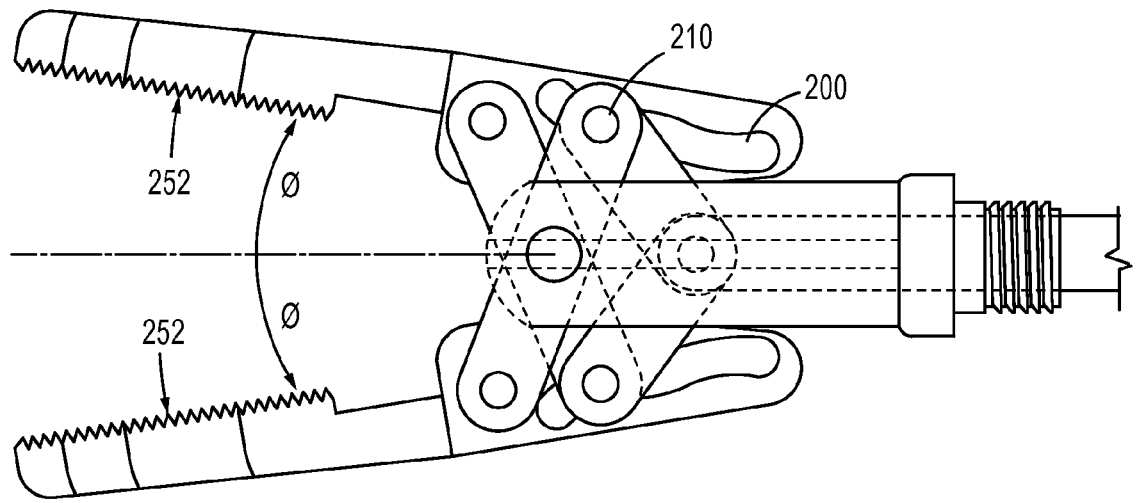
FIG. 4B shows the embodiment of FIG. 4 in a second position.

In FIG. 4B, when the movement of the actuation rod 110 has caused the connector 210 to move into section 2, the movement through the slot 200 becomes linear and the movement of the jaw faces are in a parallel direction. In other words, the angle θ remains constant through this section 2 while the distance between the jaw faces 252 becomes smaller.

Figure 4C:
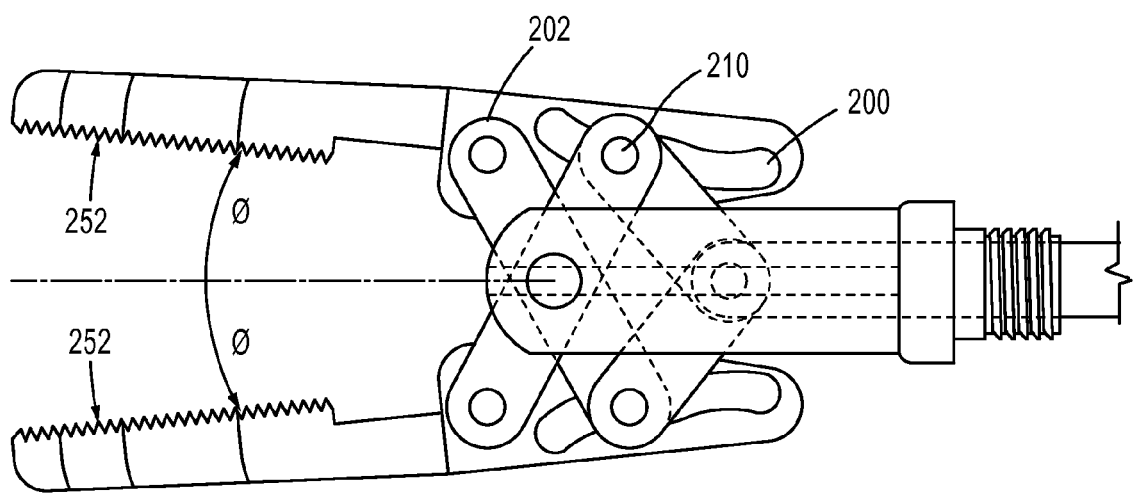
FIG. 4C shows the embodiment of FIG. 4 in a third position.

In FIG. 4C, when the movement of the actuation rod 110 has caused the connector 210 to move into section 3, the movement through slot 200 becomes angular again due to the radial shape of section 3 in the slot 200. The angle θ between the jaw faces 252 in further reduced as the actuation rod moves the connector 210 through this section 3. In this specific embodiment, once the connector has reached the end of section 3, the jaws are in a parallel relationship to each other (θ is zero) while still being separated from each other by some distance.

Figure 4D:
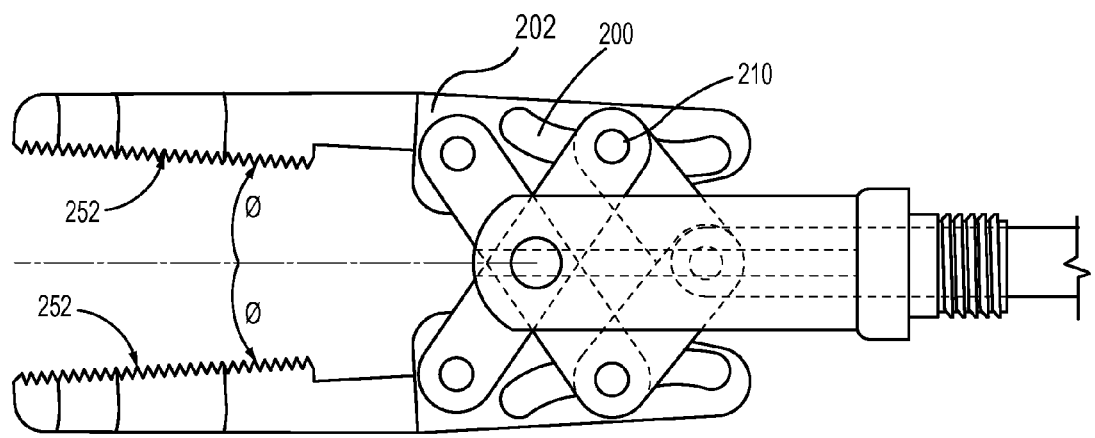
FIG. 4D shows the embodiment of FIG. 4 in a fourth position.
Figure 4E:
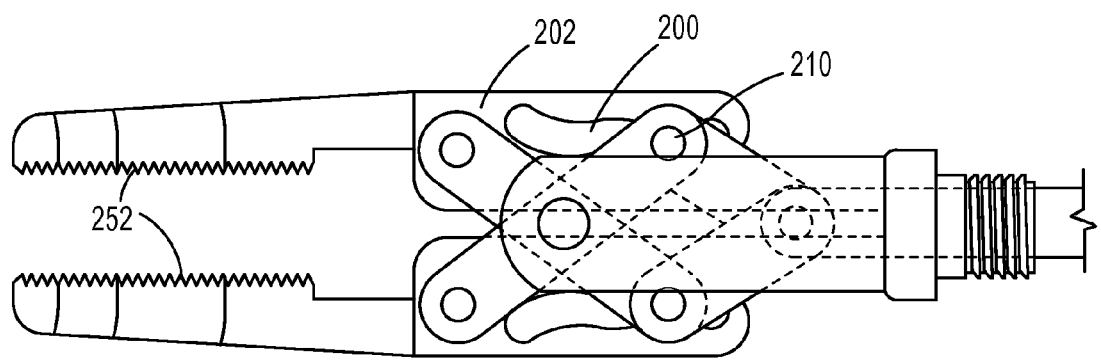
FIG. 4E shows the embodiment of FIG. 4 in a fifth position.

FIG. 4D represents the jaw position at the start of section 3 and FIG. 4E represents the jaw position at the end of section 3/beginning of section 4.

Figure 4F:
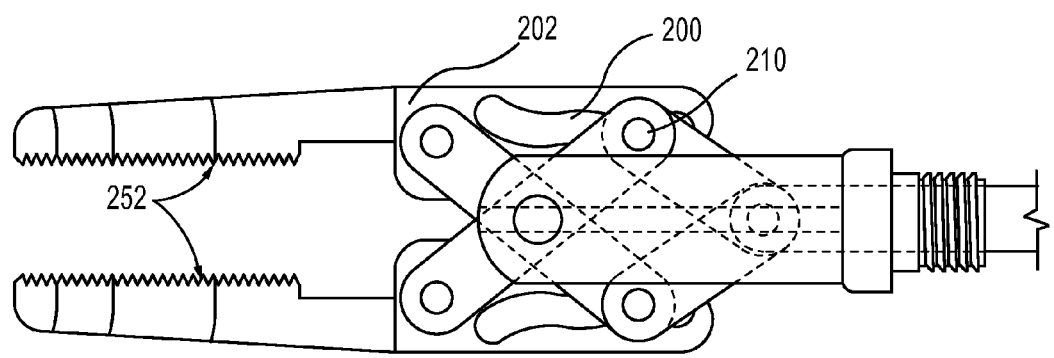
FIG. 4F shows the embodiment of FIG. 4 in a sixth position.

As shown in FIG. 4F, when the movement of the actuation rod 110 has caused the connector 210 to move into section 4, the movement through the slot 200 becomes linear again and the movement of the jaw faces are again in a parallel direction. In other words, the distance between the jaw faces 252 becomes smaller as the device is moved through section 4.

Figure 4G:
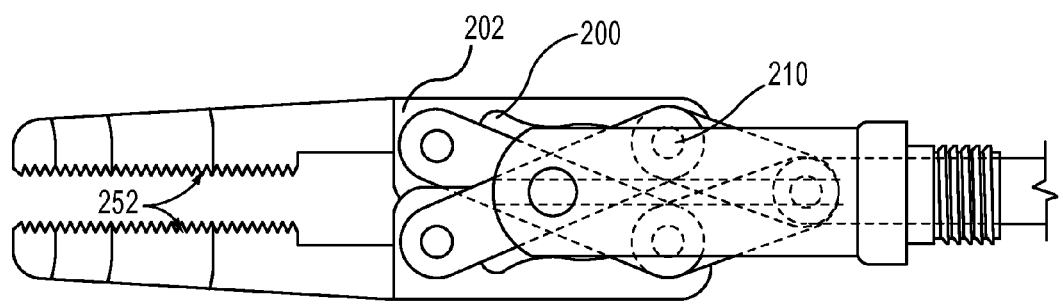
FIG. 4G shows the embodiment of FIG. 4 in a seventh position.

Finally, in FIG. 4G, due to the geometry of the last section 5 of the slot 200, the jaws begin to move away from each other as the actuation rod moves the connector 210 through section 5 of the slot 200. Note that in this example, if section 5 were to have curved in the opposition direction, the jaws would have moved toward each other rather than away from each other.

The examples shown in connection with FIGS. 4A-4G are merely one set of illustrations of the many complex movements that can be achieved by varying the geometry of the components and the slot in particular.

Each of the rotation points described in connection with the previous embodiments (e.g. 142, 144, 146 and 140) may also be constructed of anything that provides for rotation such as rivets, pins, bearings, living hinges, etc. As long as the connection points are allowed to rotate, the design will function as described above. For the connection points 142 and 144, the same rotatable criteria exists but the connection mechanism must also be able to slide within the confines of slots 126a and 126b.

Figure 5:
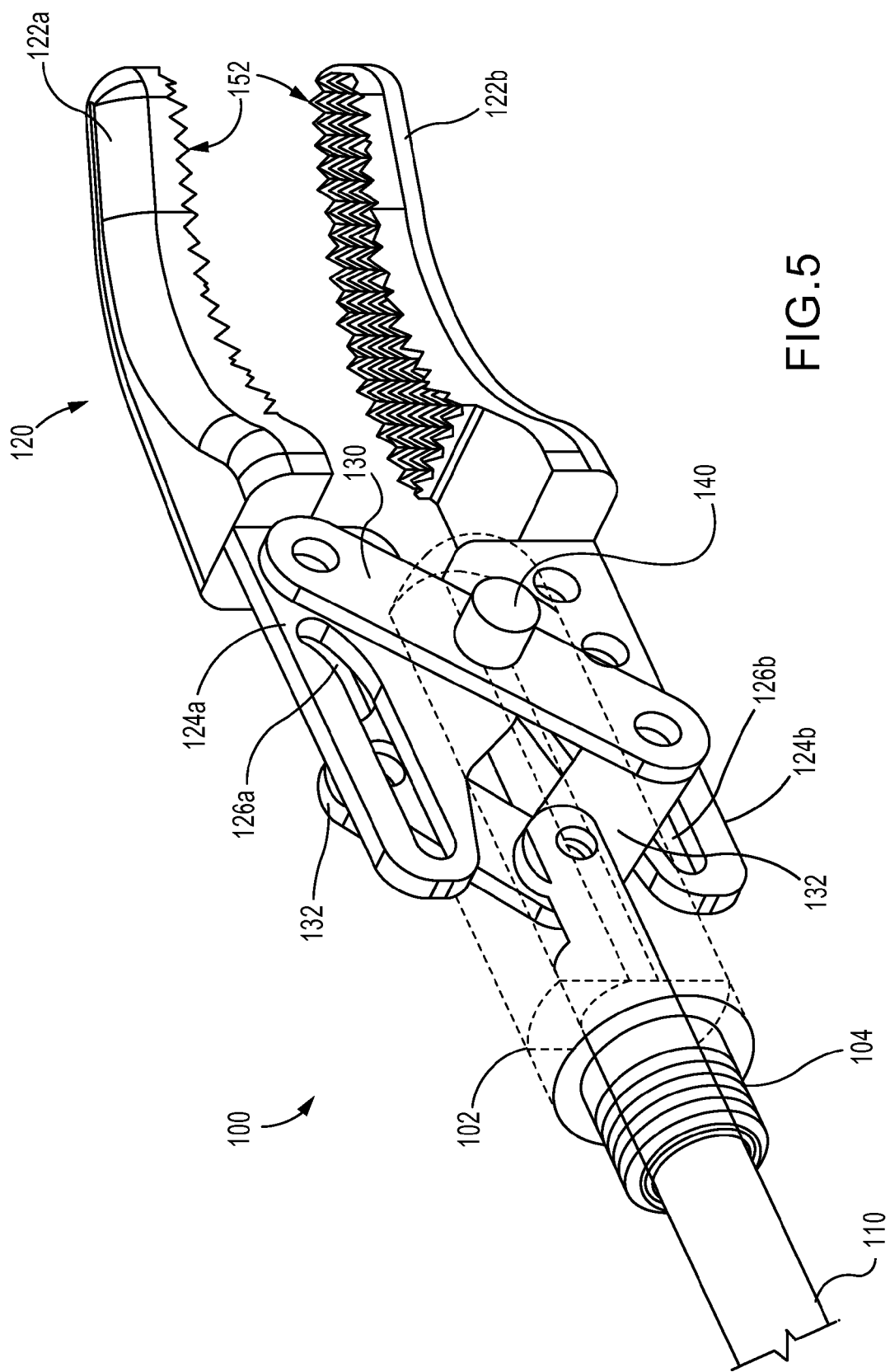
FIG. 5 is another embodiment of a device constructed in accordance with aspects of the present invention.

FIG. 5A shows a three dimensional perspective view of the embodiment of FIG. 1 illustrating in greater detail the connections between the actuation rod 110 and the actuation links 132 and the relation between the actuation links 132, the pivot links 130 and the mounting slots 126a and 126b on the grasper 120. FIG. 5B shows a top down view of the same device and embodiment from FIG. 1.

Figure 6:
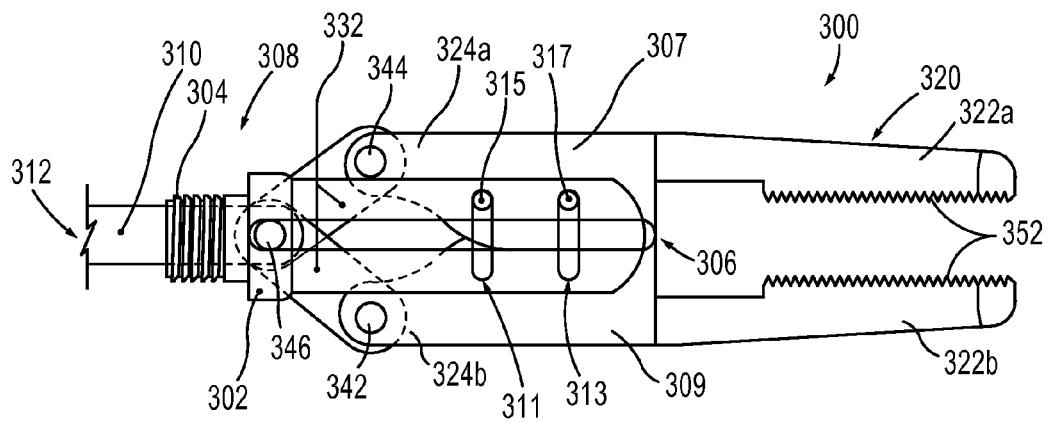
FIG. 6 is another embodiment of a device constructed in accordance with aspects of the present invention.

In accordance with another embodiment, the same type of combined parallel and angular movement between the faces of an end effector tool (for example, a grasper) can be achieved with a cam system as described below. With reference to FIG. 6, a surgical tool 300 includes a housing 302 with a generally circular cross section. A proximal end 308 of the housing has a threaded portion 304 that is adapted to couple with the distal end of a larger instrument handle assembly known in the art and as previously described with FIG. 1. Proximate a distal end 306 of the housing 302 are a pair of cam guide channels 311 and 313 that are designed to engage with cams 315 and 317 located on the grasper or end effector body and as described in more detail below. An activation rod 310 extends through the housing 302 and couples at connector 346 with an activation mechanism within the housing 302. A proximal end 312 of the activation rod 310 is designed to extend through the larger handle assembly in order for a user to easily activate and control the motion of tool 300 and the end effector 320. As described in more detail below, one or more actuation links 332 engage with the activation rod 310 and in concert with the movement of the activation rod 310 cause the parallel and/or rotational movement of the grasper jaws 320 or other end effectors on the distal end of the tool 300.

The pair of generally opposing grasper jaws 320 is engaged with the actuation rod 310 via a pair of actuation links 332 and a pair of cams 315 and 317 on mounting portions 307 and 309 of the grasper jaw structure. The grasper jaws 320 do not have any specific configuration as the instrument 300 is contemplated to be of such a general configuration as to work with any known end effector such as graspers, scissors, and any other known surgical end effector tool. In the embodiment shown in FIG. 6, the grasper jaws 320 include opposing faces 322a and 322b that each include a gripping surface 352. Each of the faces 322a and 322b are integrated with the cams 307 and 309 respectively and may be formed separately or from a single piece of material. The cams 315 and 317 generally include means, such as a guide pin or other protrusion, for the grasper to connect to and interact with the cam guide channels 311 and 313 and the actuation rod 310.

Connecting the actuation rod 310 and housing 302 to the grasper jaws 320 (e.g. the mounting portions 324a and 324b) are a pair of actuation links 332 and a pair of cams 307 and 309. The actuation links 332 include a proximal rotation point 346 that engages with the actuation rod 310 via a connector such as a pin, hinge, pivot, or other rotatable structure. At a distal end of the actuation links 332 are another pair of connectors 342 and 344 that engage the cams 315 and 317. Pins or another structure engage the cams 315 and 317 with the cam guide channels 311 and 313 on the housing 302.

Similar to the embodiment described in conjunction with FIG. 1, the shape of the cam guide channels 311 and 313 can be altered to create different movements in the jaws and thus provide a very specific design to the grasper or other end effects with specific mechanical and operational advantages. The jaws will translate the motion of the actuation links into a jaw motion that follows the degree of freedom provided by the cam guide channels.

Figure 7A:
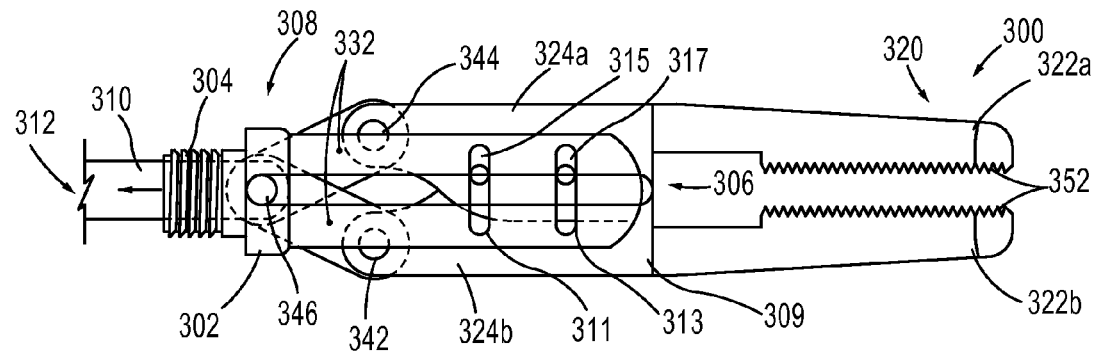
FIG. 7A is the device of FIG. 6 in a first position.
Figure 7B:
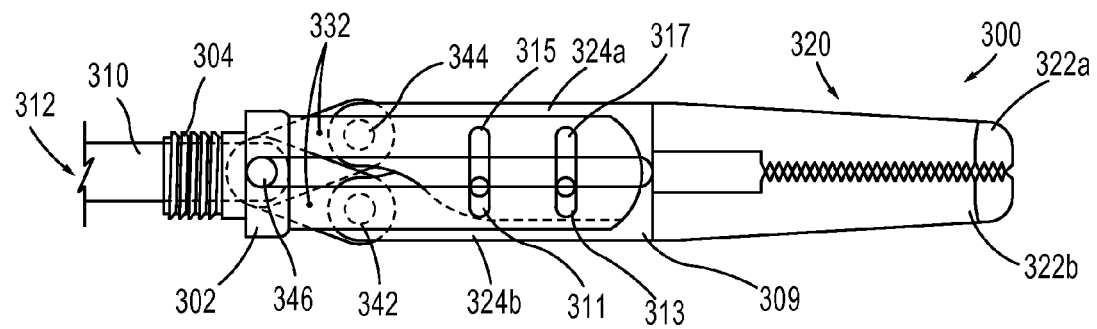
FIG. 7B is the device of FIG. 6 in a second position.

FIGS. 7A and 7B illustrate the device 300 in both its open (FIG. 7A) state and in its closed (FIG. 7B) state. As the actuation rod 310 is pulled back, the jaws begin to close in a parallel relationship because of the movement restrictions imposed by the cam guide channels 311 and 313.

Figure 8A:
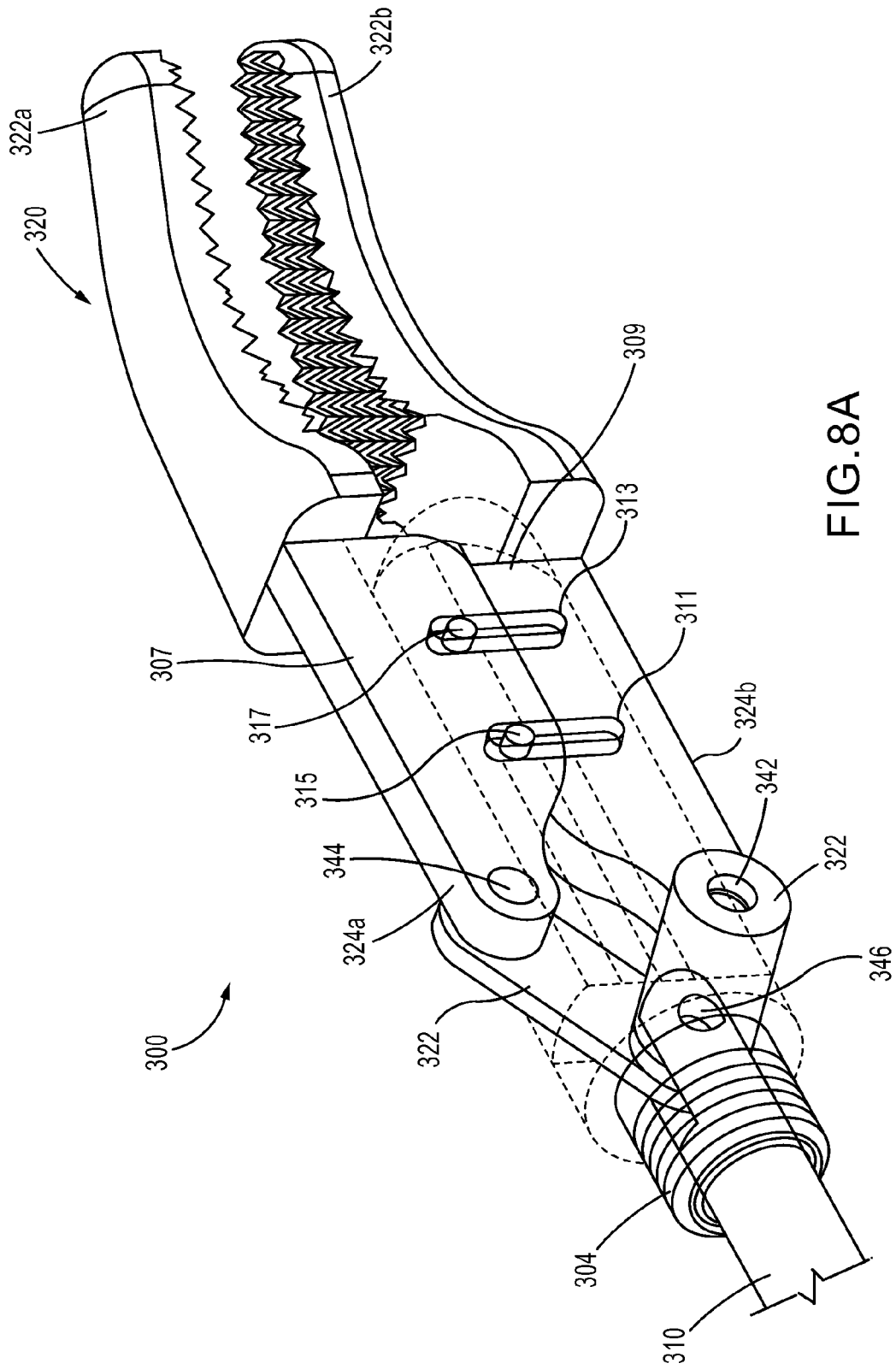
FIG. 8A is a perspective view of the device shown in FIG. 6.
Figure 8B:
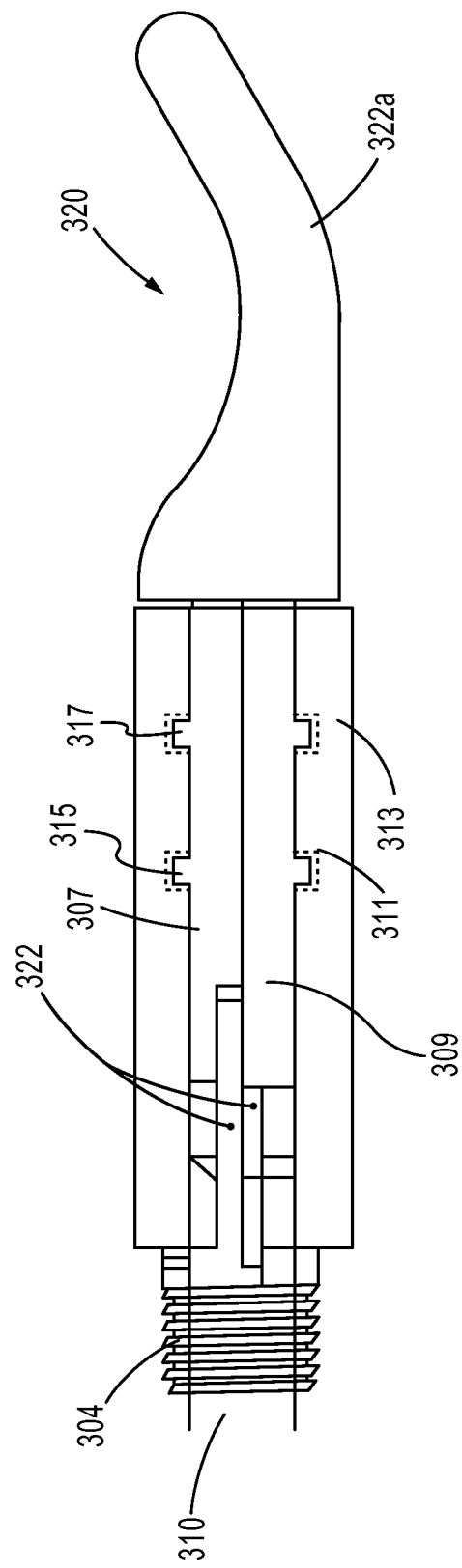
FIG. 8B is a top view of the device shown in FIG. 6.

FIG. 8A shows a three dimensional perspective of the embodiment of FIG. 6 illustrating in greater detail the connections between the actuation rod 310 and the actuation links 332 as well as the relation between the actuation links 332, the cams 315 and 317 and the cam guide channels 311 and 313. FIG. 8B shows a top down view of the same device and embodiment from FIG. 6.

Turning again to the embodiment shown in connection with FIG. 1, the design that is illustrated assumes that the pivot links 130 are sized with a substantially uniform geometry. That is the distance between the connector 142 and the fulcrum 140 is substantially equal to the distance between the connector 144 and the fulcrum. This relationship allows the centerline of the mounting slots 126a and 126b to be the same as the "y" location of the center of the distal rotation point (i.e. connectors 142). However, if the pivot links are sized with a different relative geometry such as shown in FIG. 9, then the "y" location of the distal rotation point of the mounting slot's centerline must be changed accordingly in order to maintain parallel motion between the jaw faces.

Figure 9A:
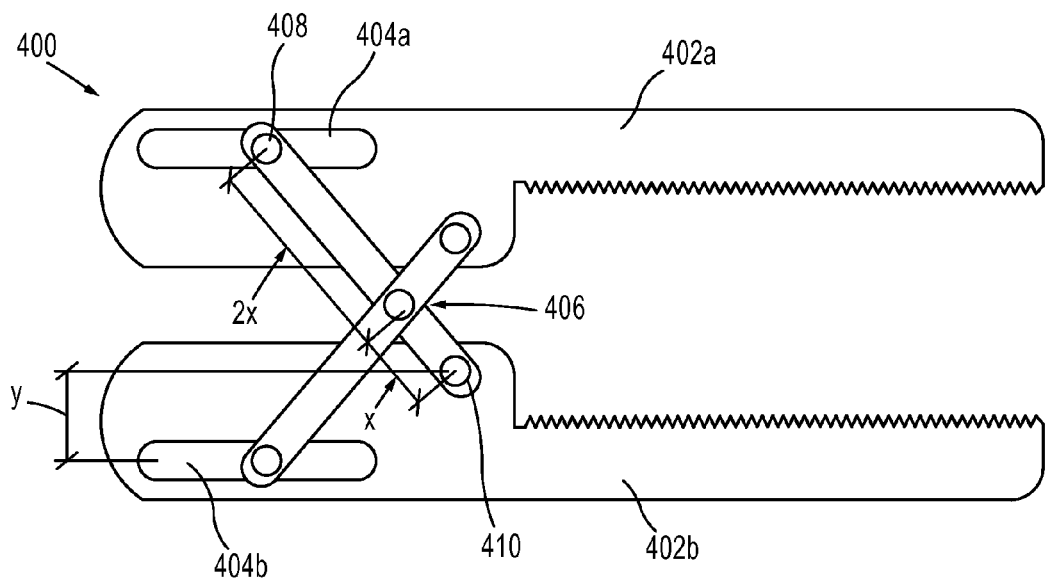
FIGS. 9A and 9B show another embodiment of a device constructed in accordance with aspects of the present invention.
Figure 9B:
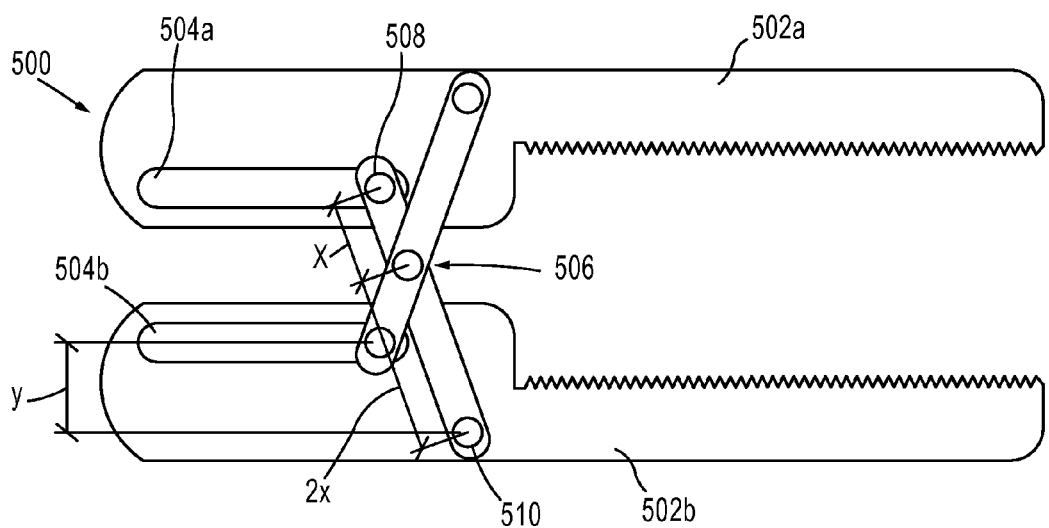

FIGS. 9A and 9B show two examples of how the relationship between the mounting slot location and the geometry of the pivot link connection points can be altered in order to achieve parallel movement of the grasper faces. In the embodiments of FIGS. 9A and 9B, the distance between the pivot link connection points and the fulcrum point are not equal and are shown as being in a 2 to 1 relationship with each other (alternate relationship in the respective figures).

As shown in FIG. 9A, in order to maintain a parallel movement for a linearly shaped slot 404a and 404b, the "y" location of the distal rotation point 410 relative to the "y" location point of the slot's centerline must be changed accordingly. The pivot link configuration example of FIG. 9A results in the slots being located further apart than the distal rotation point 410. The pivot link configuration example of FIG. 9B results in the slots being located closer together than the distal rotation point 410.

If the pivot links are not sized as described above for parallel motion then the movement of the jaws will not be parallel. Instead the jaws will move up and down but will also include an angle between the faces. As can be appreciated, many different combinations of these linkages and the slot/distal rotation points can be used to create the same effect of parallel jaw motion.

Figure 10:
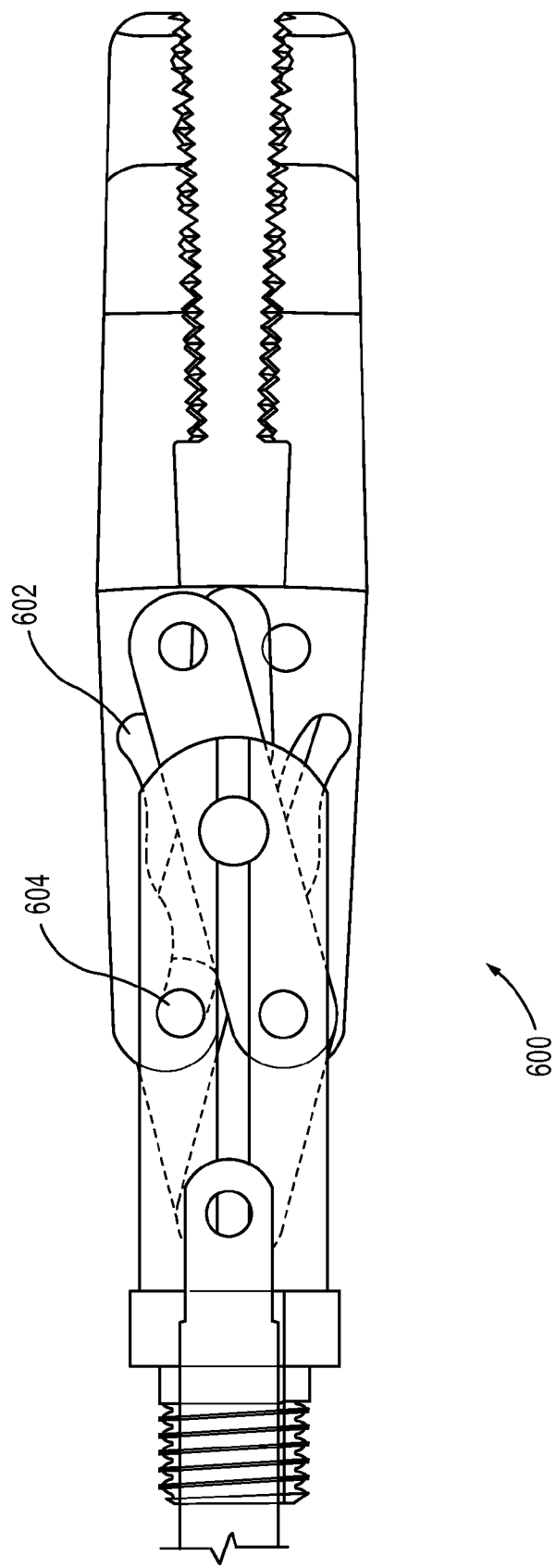
FIG. 10 is another embodiment of a device constructed in accordance with aspects of the present invention.

FIG. 10 shows an alternate embodiment of a surgical instrument 600 where a positioning slot 602 may be formatted so that it creates a locking mechanism for the surgical tool. The grasper can be fully or partially locked in place by including a radial section 604 of the slot at the end of the stroke. The radial section 604 would cause the grasper jaws to rotate away from each other, a small amount, at the closed position. When grasping tissue tightly, the tissue is always trying to open the jaws when you are grasping it. If this is allowed to happen a small amount at the fully closed position, then the jaws would lock. In order to unlock, the tissue needs to be further compressed in order to be able to get to the part of the slot that would allow the jaws to fully open.

In another embodiment that may be implemented with any of the foregoing examples, it is contemplated that the opposing faces of the end effector do not both need to move during the actuation of the device. For example, one of the end effector faces, or jaws, may be fixed so that a single action device is created. The opposing faces of the end effector may still be adapted to be maintained in a generally parallel orientation during a first part of the grasping motion, and maintained in a substantially angular orientation for at least a second portion of the grasping motion.

Those skilled in the art can readily recognize that numerous variations and substitutions may be made in the invention, its use, and its configuration to achieve substantially the same results as achieved by the embodiments described herein. Accordingly, there is no intention to limit the invention to the disclosed embodiments. Many variations, modifications and alternative constructions fall within the scope and spirit of the disclosed invention as expressed in the claims.

For example aspects of the invention relate to the orientation and capabilities of the jaws and allow a user to apply a more uniform grasping pressure across tissue than conventional (purely angular motion) graspers. With angular motion graspers, the base of the jaws squeeze much tighter than the tips of the jaws due to the difference in distance between the jaws when open at some angular displacement.

Easier visualization and depth perception—The uniform distance between the jaws allows a user to have a more controlled manipulation of tissue; that is, alignment of the tissue in the jaws and depth perception of where the tissue is sitting in the jaws is not an issue. The jaws are the same distance from each other along their entire length.

Uniform heating effect—Devices constructed in accordance with aspects disclosed herein allow for a more uniform coagulation of vessels because of the uniform distance between the jaws and because of uniform compression leading to uniform current density.

Grasping larger volumes of tissue—Along with the more controlled manipulation is the ability to grasp larger volumes of tissue between the jaws when they are open the same distance.

Larger jaw opening—The angular displacement of the jaws (at the end of the opening motion) allows the parallel jaws to get the tips much wider than is possible with a simple parallel motion. This is due to the linkage involved in the parallel motion. The more the jaws open, the longer the linkage has to be and thus the larger the trocar cannula the instrument would have to fit into. By adding this angular movement towards the end of the instrument motion, the jaws can now fit within a smaller trocar cannula but still open very wide at the tip to aid with dissection and get around larger tissue areas for grasping. It is at the end of the opening motion that the jaws become significantly non-parallel with the tips opening angularly. Thus, whenever the tissue is fully grasped and in condition for the power to be applied, the jaws have become functionally parallel even though they might be slightly non-parallel.

A parallel jaw grasper will be less likely to become fouled with tissue from a prior coagulation when several coagulations are being performed in a sequence. This is because the jaws can be separated along their full length allowing tissue to be removed from one jaw using a second instrument (or by simply falling away). A conventional instrument tends to create a possibility for small amounts of tissue to become lodged near the proximal end of the jaw area.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A surgical instrument, comprising:
   a housing;
   an actuation rod extending through the housing;
   a first jaw member, the first jaw member including a first positioning slot, the first positioning slot including a linear portion and a radial portion;
   a first actuation link having a proximal end and a distal end, the proximal end of the first actuation link coupled with the actuation rod;
   a first pivot link having a proximal end and a distal end, the proximal end of the pivot link coupled with the distal end of the first actuation link, the distal end of the first pivot link coupled with the first jaw member;
   a second jaw member, the second jaw member including a second positioning slot, the second positioning slot including a linear portion and a radial portion; a second actuation link have a proximal end and a distal end, the proximal end of the second actuation link coupled with the actuation rod;
   a second pivot link having a proximal end and a distal end, the proximal end of the second pivot link coupled with the distal end of the second actuation link, the distal end of the second pivot link coupled with the second jaw member;
   wherein the proximal end of the first pivot link and the distal end of the first actuation link are slidably engaged within the first positioning slot; and wherein the proximal end of the second pivot link and the distal end of the second actuation link are slidably engaged within the second positioning slot.

2. The surgical instrument of claim 1, wherein the first jaw member includes a grasping portion and a mounting portion, wherein the first positioning slot is located within the mounting portion.

3. The surgical instrument of claim 2, wherein the grasping portion and the mounting portion are integrated with each other.

4. The surgical instrument of claim 1, further comprising a handle assembly connected to the housing.

5. The surgical instrument of claim 4, wherein the handle assembly is coupled to the actuation rod so as to control the linear motion of the actuation rod.

6. The surgical instrument of claim 1, wherein movement of the distal end of the first actuation link and the proximal end of the first pivot link within the linear portion of the first positioning slot moves the first jaw member in an axial motion and wherein movement of the distal end of the first actuation link and the proximal end of the first pivot link within the radial portion of the first positioning slot moves the first jaw member in an angular motion.

7. The surgical instrument of claim 1, wherein the first positioning slot includes a plurality of linear portions.

8. The surgical instrument of claim 1, wherein the first positioning slot includes a plurality of radial portions.

9. The surgical instrument of claim 1, wherein the distal end of the first actuation link and the proximal end of the first pivot link are connected by a fastener.

10. The surgical instrument of claim 9, wherein the fastener is selected from the group consisting of a pin, a rivet, a hinge, a living hinge, and a dowel.

11. The surgical instrument of claim 1, wherein the housing includes a fulcrum connection point and wherein the pivot link is coupled with the fulcrum connection point.

12. The surgical instrument of claim 11, wherein the first pivot link is coupled to the fulcrum connection point at a point that is generally equidistant from the first pivot link proximal end and the first pivot link distal end.

13. A surgical instrument actuation device, comprising:
   an end effector, the end effector including a first positioning slot and a second positioning slot, the first positioning slot including a first linear portion and a first radial portion and the second positioning slot including a second linear portion and a second radial portion;
   an actuation link having a proximal end and a distal end, the proximal end of the actuation link coupled with an actuator of the surgical tool;
   a pivot link having a proximal end and a distal end, the proximal end of the pivot link coupled with distal end of the actuation link, the distal end of the pivot link coupled with the end effector;
   wherein the proximal end of the pivot link and the distal end of the actuation link are slidably engaged with at least the first positioning slot.

14. The surgical instrument of claim 13, wherein the end effector includes a pair of opposing faces, and wherein the opposing faces of the end effector move in a parallel manner when the proximal end of the pivot link and the distal end of the actuation link are engaged in at least the first linear portion of the first positioning slot, and wherein the opposing faces of the end effector move in an angular manner when the proximal end of the pivot link and the distal end of the actuation link are engaged with at least the first radial portion of the first positioning slot.

15. The surgical instrument of claim 13, wherein the first and second positioning slots each include plurality of linear portions and a plurality of radial portions.

* * * * *